United States Patent
Tanaka et al.

(10) Patent No.: US 10,869,596 B2
(45) Date of Patent: Dec. 22, 2020

(54) LIGHT SOURCE DEVICE FOR ENDOSCOPE AND ENDOSCOPE SYSTEM

(71) Applicant: OLYMPUS CORPORATION, Tokyo (JP)

(72) Inventors: Satoshi Tanaka, Hachioji (JP); Yusuke Yabe, Chofu (JP); Tomoya Takahashi, Hachioji (JP); Masaaki Watanabe, Hachioji (JP); Susumu Hashimoto, Hachioji (JP); Yasuo Komatsu, Yokohama (JP); Manabu Yajima, Hachioji (JP); Akihiko Mochida, Hachioji (JP); Koji Omori, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 330 days.

(21) Appl. No.: 15/730,091

(22) Filed: Oct. 11, 2017

(65) Prior Publication Data

US 2018/0042470 A1 Feb. 15, 2018

Related U.S. Application Data

(63) Continuation of application No. PCT/JP2016/079791, filed on Oct. 6, 2016.

(30) Foreign Application Priority Data

Oct. 14, 2015 (JP) .................. 2015-203004

(51) Int. Cl.
*A61B 1/06* (2006.01)
*G02B 23/24* (2006.01)
(Continued)

(52) U.S. Cl.
CPC ........ *A61B 1/0676* (2013.01); *A61B 1/00096* (2013.01); *A61B 1/06* (2013.01);
(Continued)

(58) Field of Classification Search
CPC .. F21K 9/64; F21V 9/32; G02B 23/24; G02B 23/2461; G02B 23/2484
See application file for complete search history.

(56) References Cited

U.S. PATENT DOCUMENTS

2011/0034770 A1 2/2011 Endo et al.
2011/0149549 A1* 6/2011 Miyake ................. F21K 9/64
362/84

(Continued)

FOREIGN PATENT DOCUMENTS

EP 2283769 A1 2/2011
JP 2011-036361 A 2/2011
(Continued)

OTHER PUBLICATIONS

Machine Language Translation of JP 2013-215435 A, Yabe, Oct. 24, 2013.*
(Continued)

*Primary Examiner* — John P Leubecker
*Assistant Examiner* — Minqiao Huang
(74) *Attorney, Agent, or Firm* — Scully, Scott, Murphy & Presser, P.C.

(57) ABSTRACT

A light source device for endoscope includes: an irradiation portion capable of radiating excitation light; a rotating body provided on an optical axis of the excitation light and configured to rotate with a rotating shaft as a center; a phosphor arranged in an irradiation area of the excitation light, and configured to generate fluorescence by being irradiated with the excitation light; a light quantity control portion configured to control irradiation intensity or irradiation time of the excitation light; and a rotation control portion configured to rotate the rotating body at a predetermined speed when the excitation light is radiated with a first irradiation intensity or time and rotate the rotating body faster than the predetermined speed when reducing the (Continued)

irradiation intensity or the irradiation time of the excitation light is reduced in the irradiation intensity or time vis-a-vis the first ones.

7 Claims, 12 Drawing Sheets

(51) Int. Cl.
 *F21V 9/32* (2018.01)
 *F21K 9/64* (2016.01)
 *A61B 1/00* (2006.01)

(52) U.S. Cl.
 CPC .......... *A61B 1/0638* (2013.01); *A61B 1/0646* (2013.01); *A61B 1/0653* (2013.01); *A61B 1/0669* (2013.01); *F21K 9/64* (2016.08); *F21V 9/32* (2018.02); *G02B 23/24* (2013.01); *G02B 23/2461* (2013.01); *G02B 23/2484* (2013.01)

(56) References Cited

U.S. PATENT DOCUMENTS

| | | | | |
|---|---|---|---|---|
| 2013/0100644 A1* | 4/2013 | Hu | ............................. | F21V 9/32 362/84 |
| 2014/0254129 A1* | 9/2014 | Miyoshi | ................. | F21V 13/08 362/84 |
| 2014/0347634 A1* | 11/2014 | Bommerbach | ...... | H04N 9/3158 353/31 |
| 2014/0362558 A1* | 12/2014 | Nauen | ..................... | F21V 14/08 362/84 |
| 2015/0099932 A1* | 4/2015 | Morimoto | ............ | A61B 1/0661 600/180 |
| 2015/0219870 A1* | 8/2015 | Adema | .................. | G02B 7/006 359/892 |
| 2016/0150200 A1* | 5/2016 | Saka | ..................... | G03B 21/005 353/31 |
| 2016/0349605 A1* | 12/2016 | Kitade | ................. | G03B 21/204 |
| 2017/0032985 A1* | 2/2017 | Ryo | ................. | H01L 21/67051 |
| 2018/0196335 A1* | 7/2018 | Kato | ..................... | G03B 21/00 |

FOREIGN PATENT DOCUMENTS

| | | |
|---|---|---|
| JP | 2011-145681 A | 7/2011 |
| JP | 2013-215435 A | 10/2013 |
| JP | 2015-116378 A | 6/2015 |

OTHER PUBLICATIONS

International Search Report dated Dec. 13, 2016 issued in PCT/JP2016/079791.

* cited by examiner

LIGHT SOURCE DEVICE FOR ENDOSCOPE AND ENDOSCOPE SYSTEM

CROSS REFERENCE TO RELATED APPLICATION

This application is a continuation application of PCT/JP2016/079791 filed on Oct. 6, 2016 and claims benefit of Japanese Application No. 2015-203004 filed in Japan on Oct. 14, 2015, the entire contents of which are incorporated herein by this reference.

BACKGROUND OF THE INVENTION

1. Field of the Invention

The present invention relates to a light source device for endoscope and an endoscope system including a rotating body provided with a phosphor configured to receive light radiated from an excitation light irradiation portion and make light of a predetermined wavelength region be emitted.

2. Description of the Related Art

Conventionally, endoscopes configured including an insertion portion in an elongated tubular shape have been widely utilized in a medical field and an industrial field for example. Among the endoscopes, a medical endoscope used in the medical field is configured such that an internal organ or the like is observed by inserting an insertion portion into a subject, a body of a living body for example, and various kinds of treatment can be performed on the internal organ or the like by using a treatment instrument inserted into a treatment instrument insertion channel provided in the endoscope as needed. In addition, an industrial endoscope used in the industrial field is configured such that, by inserting the insertion portion to a subject, an inside of a device or machinery or the like such as a jet engine or factory piping for example, a state such as a scratch or corrosion inside the subject can be observed and inspected or the like.

An environment in which the endoscope is used sometimes a dark environment without a presence of ambient light, such as the inside of a body cavity of a living body or the inside of piping of machinery. In order to acquire an endoscopic image even in such an environment, an endoscope system configured including an illumination unit for radiating illumination light from a distal end portion of an endoscope toward an outer front part or side part or the like and a light source device that supplies light from outside to the illumination unit for example is well-known.

Some of the light source devices for endoscope applied to conventional endoscope systems of such a form are configured so as to emit not only normal white illumination light but also the illumination light of different wavelengths according to a use of the endoscope. For example, various kinds of the light source device for endoscope that use an excitation light source (excitation light irradiation portion or illumination portion) capable of radiating excitation light (laser) and a phosphor wheel (rotating body) which receives the excitation light and rotationally drives a phosphor which emits fluorescence to emit the excitation light as the illumination light have been proposed and put into practical use.

For example, the light source device for endoscope disclosed by Japanese Patent Application Laid-Open Publication No. 2013-215435 includes a configuration of controlling a rotation number of a rotating body based on a drive voltage or a light quantity value of a light source for example in order to suppress degradation of a phosphor due to excitation light (laser) radiated from an excitation light radiation portion.

More specifically, for example, while control is performed to increase a rotation cycle (raise a rotation number) of the rotating body in a case of increasing irradiation intensity or irradiation time of the excitation light and performing irradiation with the illumination light in a large light quantity in order to perform far point observation, rotation control is performed to reduce the rotation cycle (lower the rotation number) of the rotating body in the case of reducing the irradiation intensity or the irradiation time of the excitation light and performing the irradiation with the illumination light in a small light quantity when performing near point observation. By the configuration, in the light source device for endoscope disclosed by Japanese Patent Application Laid-Open Publication No. 2013-215435 described above or the like, during large light quantity irradiation that greatly affects the phosphor, the degradation of the phosphor is prevented by increasing the rotation cycle of the rotating body.

On the other hand, in conventional light source devices for endoscope of this kind, an irradiation position of the excitation light to the phosphor provided on the rotating body is cyclically changed due to a rotation mechanism (rotational deflection of a rotating shaft or attachment inaccuracy of the rotating body or the like) of the rotating body for example, and the light quantity of the fluorescence emitted from the phosphor may cyclically may fluctuate. However, light quantity fluctuation is not taken into consideration in the light source device for endoscope disclosed by Japanese Patent Application Laid-Open Publication No. 2013-215435 described above or the like.

Then, the light source device for endoscope disclosed by Japanese Patent Application Laid-Open Publication No. 2015-116378 for example includes the configuration of acquiring light quantity fluctuation data indicating a relation between a rotating position in a diameter direction of a phosphor wheel (rotating body) and a light quantity beforehand and using such data to control the light quantity of excitation light by reverse phase control for example, in order to suppress light quantity fluctuation accompanying rotation of the phosphor wheel (rotating body), in a light source that irradiates the phosphor wheel (rotating body) with the excitation light to generate fluorescence.

SUMMARY OF THE INVENTION

A light source device for endoscope of one aspect of the present invention includes: an irradiation portion capable of radiating excitation light; a rotating body provided on an optical axis of the excitation light and configured to rotate with a rotating shaft as a center; a phosphor arranged in an irradiation area of the excitation light in the rotating body, and configured to generate fluorescence by being irradiated with the excitation light; a light quantity control portion configured to control irradiation intensity or irradiation time of the excitation light; and a rotation control portion configured to perform rotation control of rotating the rotating body at a predetermined speed when causing the irradiation intensity or the irradiation time of the excitation light to be a first irradiation intensity or a first irradiation time by the light quantity control portion, and perform rotation control of rotating the rotating body faster than the predetermined speed when making the irradiation intensity less than the first irradiation intensity or making the irradiation time of the excitation light shorter than the first irradiation time by the light quantity control portion.

In addition, an endoscope system of one aspect of the present invention includes: the light source device for endoscope; an endoscope including a light guide portion configured to guide the fluorescence generated from the phosphor and irradiate a subject with the fluorescence, and an image pickup portion configured to receive light from the subject and generate an image pickup signal of the subject; an image generation portion configured to generate an observation image of the subject from the image pickup signal of the subject generated by the image pickup portion; and a brightness detection portion configured to detect brightness of the observation image generated by the image generation portion, and the light quantity control portion controls the irradiation intensity or the irradiation time of the excitation light in order to make the observation image have a predetermined brightness based on a brightness detection result by the brightness detection portion.

DETAILED DESCRIPTION OF THE PREFERRED EMBODIMENT(S)

Hereinafter, the present invention will be described by illustrated embodiments. The respective drawings used in the following description are schematic, and dimensional relations and scales or the like of respective members are sometimes differently illustrated for each of respective components in order to illustrate the respective components in such sizes that the respective components can be recognized on the drawings. Therefore, the present invention is not limited only to an illustrated form, regarding quantities of the components, shapes of the components, ratios of the sizes of the components and relative positional relations of the respective components described in the respective drawings.

First Embodiment

Figure 1:
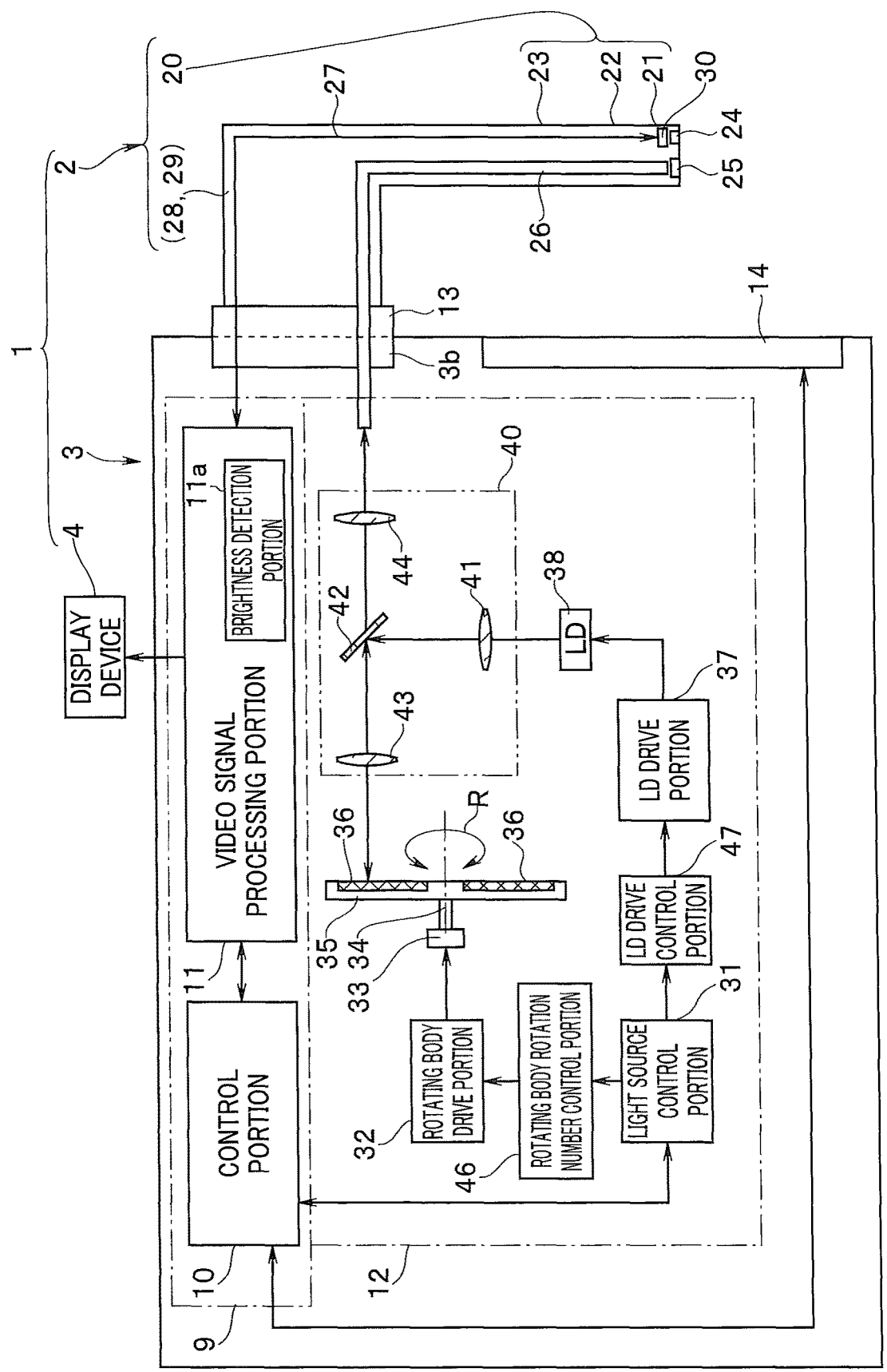
FIG. 1 is a block configuration diagram illustrating a schematic configuration of an endoscope system including a light source device for endoscope in a first embodiment of the present invention.

FIG. 1 is a block configuration diagram illustrating a schematic configuration of an endoscope system including a light source device for endoscope in the first embodiment of the present invention. First, the overall schematic configuration of the endoscope system including the light source device for endoscope in the present embodiment will be described below using FIG. 1.

An endoscope system 1 is, as illustrated in FIG. 1, mainly configured including an endoscope 2, a control unit 3, and a display device 4. The endoscope 2 is configured to be freely attachable and detachable to/from a connector portion 3b (to be described later) of the control unit 3 through a connector 13 (to be described later).

Note that, for the endoscope 2 itself applied in the present embodiment, the endoscope that is conventionally and generally put to practical use and widespread is applicable as it is. Therefore, for the configuration of the endoscope 2 itself, an illustration is simplified, detailed description is omitted for respective components, and only essential components concerning the present invention will be described.

The endoscope 2 is a configuration unit configured to have an inside of a body cavity as an observation target for example, pick up and image of the observation target and output an image pickup signal. The endoscope 2 is configured including an elongated insertion portion 20 capable of being inserted into the body cavity, an operation portion 28 connected to a proximal end side of the insertion portion 20, a universal cable 29 extended from the operation portion 28, and the connector 13 provided on a distal end of the universal cable 29, etc.

The insertion portion 20 forms an elongated tubular shape by connecting a distal end portion 21, a bending portion 22 and a flexible tube portion 23 in order from a distal end side. Into the inside of the insertion portion 20, a light guide 26 and a signal line 27 or the like are inserted (details are to be described later). The distal end portion 21 is provided with an illumination lens 25, an image pickup objective lens 24, and an image pickup unit 30, etc.

The illumination lens 25 is an optical lens configured to converge illumination light transmitted from a light source unit 12 (to be described later) by the light guide 26 (to be described later) and emit the illumination light from a front surface of the distal end portion 21 to front. Therefore, on a rear end face of the illumination lens 25, a distal end face of the light guide 26 that guides the illumination light for illuminating the observation target from the light source unit 12 (details are to be described later) to the distal end of the insertion portion 20 is disposed. Describing in more detail, the light guide 26 is a light guide portion configured to guide fluorescence generated from a phosphor 36 in the light source unit 12 to be described later and irradiate a subject which is the observation target present in an area facing the distal end face of the distal end portion 21 with the fluorescence.

The light guide 26 is inserted into the insertion portion 20, the operation portion 28 and the universal cable 29, and connected through the connector 13 and the connector portion 3b to the light source unit 12 (to be described later) inside the control unit 3. By such a configuration, the illumination light emitted from the light source unit 12 is supplied through the light guide 26 to the illumination lens 25, and is emitted from the illumination lens 25 to the front of the endoscope 2. Thus, the subject which is the observation target present in the area facing the distal end face of the distal end portion 21 of the insertion portion 20 of the endoscope 2 is illuminated.

In addition, the image pickup objective lens 24 is an optical lens configured to receive light illuminated by the illumination light from the illumination lens 25 and reflected by the subject and make an optical image be formed. The image pickup objective lens 24 is disposed adjacently to the illumination lens 25 for example, on the front surface of the distal end portion 21. At an image forming position behind the image pickup objective lens 24, the image pickup unit 30 is disposed.

The image pickup unit 30 is a configuration unit which is an image pickup portion including an image pickup device (not illustrated) which is an electronic component that receives an optical image of the subject formed by the image pickup objective lens 24, performs photoelectric conversion processing and generates the image pickup signal of the subject or the like.

Note that, as the image pickup device (not illustrated), a photoelectric conversion element or the like such as a CCD (charge coupled device) image sensor or a CMOS (complementary metal oxide semiconductor) type image sensor is applied. Then, from the image pickup unit 30, the signal line 27 is extended inside the insertion portion 20 to a back, and the signal line 27 is inserted through the insertion portion 20, the operation portion 28 and the universal cable 29, and connected through the connector 13 and the connector portion 3b to a video signal processing portion 11 (to be described later) inside the control unit 3. By the configuration, the image pickup signal generated by the image pickup device of the image pickup unit 30 is transmitted through the signal line 27 to the video signal processing portion 11. The other components of the endoscope 2 are almost similar to the components of the conventional and general endoscope.

The control unit 3 is configured including a signal processing control unit 9 which is a signal processing control portion formed of a control portion 10 and the video signal processing portion 11, the light source unit 12 which is the light source device for endoscope, the connector portion 3b, and an operation panel 14, etc.

Note that, in the present embodiment, a form that the signal processing control unit 9 and the light source unit 12 are configured inside a same housing is illustrated. However, the form is not limited to such a form. For example, the form may be such that the signal processing control unit 9 and the light source unit 12 are configured in separate bodies respectively and connected with each other by a cable.

The connector portion 3b and the operation panel 14 are components provided on a housing front surface of the control unit 3. The connector portion 3b is a connection portion configured to connect the control unit 3 and the endoscope 2 when the connector 13 of the universal cable 29 is mounted. In addition, the operation panel 14 includes a plurality of various kinds of operation members for receiving an operation of a user, and is a configuration portion configured by a circuit board or the like (not illustrated) configured to receive the operation of the plurality of operation members and output respective predetermined instruction signals.

The control portion 10 in the signal processing control unit 9 is a control unit configured to generally control the entire present endoscope system 1. The control portion 10 is electrically connected with the respective configuration units of the present endoscope system 1, and performs various kinds of control by outputting a predetermined control signal appropriately at predetermined timing. In addition, the control portion 10 is electrically connected with the operation panel 14, and the instruction signal from the operation panel 14 is inputted. The control portion 10 receives the various kinds of instruction signals that are inputted, and appropriately controls the corresponding configuration unit.

The video signal processing portion 11 in the signal processing control unit 9 is an image generation portion configured to receive the image pickup signal of the subject generated and outputted by the image pickup unit 30 (image pickup portion) of the endoscope 2, convert the image pickup signal to a predetermined video signal and generate an observation image of the subject. The video signal generated in the signal processing control unit 9 is outputted to the display device 4, and is displayed as a video image expressing an endoscopic image.

Further, the video signal processing portion 11 is configured including a brightness detection portion 11a. The brightness detection portion 11a is a configuration unit formed of an electric component and a circuit portion configured to detect brightness of the observation image displayed based on the video signal generated by the video signal processing portion 11 (image generation portion) as described above.

The display device 4 is a configuration unit for displaying an image according to the video signal outputted from the video signal processing portion 11. As the display device 4, other than a liquid crystal display (LCD) device and an organic electro-luminescence (OEL) display device for example, an image receiver using a cathode ray tube (CRT) or the like is applied.

The light source unit 12 which is the light source device for endoscope is a configuration unit configured to supply the illumination light for illuminating the observation target through the light guide 26 to the illumination lens 25 at the distal end portion 21 of the endoscope 2.

The light source unit 12 which is the light source device for endoscope in the endoscope system in the present embodiment is mainly configured by a light source control portion 31, a rotating body rotation number control portion 46, a rotating body drive portion 32, a rotating body drive motor 33, a rotating body rotating shaft 34, a fluorescent wheel 35 which is a rotating body, the phosphor 36, a light emission drive control portion (abbreviated as an LD drive control portion in FIG. 1 and indicated similarly hereinafter)

47, a light emission drive portion (abbreviated as an LD drive portion in FIG. 1 and indicated similarly hereinafter) 37, a semiconductor laser LD (laser diode; abbreviated as an LD in FIG. 1) 38 which is an excitation light irradiation portion (abbreviated as an irradiation portion, hereinafter), and an optical unit 40, etc.

The light source control portion 31 is a control unit configured to control the light source unit 12 under control of the control portion 10. The light source control portion 31 has a function of controlling drive of the rotating body drive portion 32 through the rotating body rotation number control portion 46 to make the rotating body drive motor 33 be driven, thereby controlling the rotation (rotation number) of the fluorescent wheel 35 (rotating body) with the rotating body rotating shaft 34 as a center for example. Here, the rotating body rotation number control portion 46 is a rotation control portion configured to perform rotation control of increasing a rotation cycle of the rotating body or rotation control of reducing the rotation cycle.

In addition, the light source control portion 31 is the light source control portion configured to control the drive of the LD drive portion 37 through the LD drive control portion 47 to drive the semiconductor laser LD 38 to emit the light, thereby controlling a light emission quantity of the excitation light from the semiconductor laser LD 38. Here, the LD drive control portion 47 has a function as a light quantity control portion configured to control irradiation intensity or irradiation time of the emission light (excitation light) of the semiconductor laser LD 38 and control the light quantity.

Specifically, for example, the LD drive control portion 47 controls the irradiation intensity or the irradiation time of the excitation light in order to make the observation image have a predetermined brightness based on a brightness detection result by the brightness detection portion 11a.

The rotating body drive portion 32 is a configuration portion including a drive circuit and a drive mechanism for driving the rotating body drive motor 33. The rotating body drive portion 32 is electrically connected with the light source control portion 31 through the rotating body rotation number control portion 46, and the drive is controlled by the rotating body rotation number control portion 46 under the control of the light source control portion 31. That is, the drive of the rotating body drive portion 32 is controlled by the rotating body rotation number control portion 46 which receives a light quantity instruction signal outputted from the light source control portion 31.

The rotating body drive motor 33 is a rotating motor connected to the fluorescent wheel 35 with the rotating body rotating shaft 34 being interposed. The rotating body drive motor 33 generates drive force to rotate the fluorescent wheel 35 in a direction of an arrow R in FIG. 1 around the rotating body rotating shaft 34.

The rotating body rotating shaft 34 is a shaft member pivotally supported integrally at a rotation center of the fluorescent wheel 35 which is the rotating body and configured to rotate the fluorescent wheel 35.

The fluorescent wheel 35 is the rotating body formed in a thin plate disk shape and configured to rotate with the rotating body rotating shaft 34 as the center. On one board surface (surface that receives the excitation light radiated from the semiconductor laser LD 38) of the fluorescent wheel 35, the phosphor 36 is provided. Then, the fluorescent wheel 35 is configured such that the phosphor 36 is irradiated with the excitation light from the semiconductor laser LD 38. That is, for that, the fluorescent wheel 35 (rotating body) is disposed on an optical axis of the excitation light.

The phosphor 36 is a light emitting body configured to be excited and emit the fluorescence when irradiated with the irradiation light (excitation light) from the semiconductor laser LD 38. The phosphor 36 is arranged in an irradiation area of the excitation light at a position on a predetermined radius from the rotating body rotating shaft 34 on the fluorescent wheel 35 (rotating body).

The LD drive portion 37 is a configuration portion controlled through the light source control portion 31 under the control of the control portion 10, for generating a semiconductor laser LD drive current for controlling the drive of the semiconductor laser LD 38, supplying the current to the semiconductor laser LD 38, and making the light of a predetermined wavelength region be emitted.

The semiconductor laser LD 38 is an irradiation portion configured to radiate the excitation light. The irradiation light (excitation light) radiated from the semiconductor laser LD 38 is configured to be radiated toward the phosphor 36 by an action of the optical unit 40 (to be described later in details).

Note that the semiconductor laser LD 38 (irradiation portion) is configured such that the light emission quantity becomes variable. That is, for the semiconductor laser LD 38, the light emission quantity of the excitation light is controlled by the LD drive control portion 47 which receives the light quantity instruction signal outputted from the light source control portion 31 for example.

The optical unit 40 is configured including a lens 41, a dichroic filter 42, a lens 43, and a lens 44.

The lens 41 is an optical lens configured to transmit the irradiation light (excitation light) from the semiconductor laser LD 38 and emit the irradiation light to the dichroic filter 42.

The dichroic filter 42 is a planar optical member having a function of receiving the irradiation light (excitation light) from the semiconductor laser LD 38 transmitted through the lens 41, reflecting the irradiation light to a side of the phosphor 36, and also transmitting the light of a specific wavelength region of the irradiation light (fluorescence) from the phosphor 36 transmitted through the lens 43 as described later. Therefore, the dichroic filter 42 is arranged by being inclined at an angle of 45 degrees relative to both of the optical axis of the lens 41 and the optical axis of the lens 43. In this case, so as to reflect the irradiation light (excitation light) from the semiconductor laser LD 38 to the side of the phosphor 36, the reflection surface is turned to the side of the phosphor 36 and arranged.

The lens 43 is an optical lens configured to transmit the irradiation light (excitation light) from the semiconductor laser LD 38 that is reflected by the dichroic filter 42, guide the irradiation light to the phosphor 36, also transmit the irradiation light (fluorescence) from the phosphor 36 and emit the irradiation light to the side of the dichroic filter 42.

The lens 44 is an optical lens configured to transmit the irradiation light (fluorescence) from the phosphor 36 advancing straight through the lens 43 and the dichroic filter 42 and emit the irradiation light toward a proximal end face of the light guide 26.

Note that, simply describing, in the light source unit 12 which is the light source device for endoscope in the present embodiment, by a rotating body unit (the rotating body drive portion 32, the rotating body drive motor 33, the rotating body rotating shaft 34, the fluorescent wheel 35 (rotating body), the phosphor 36), an LD unit (the LD drive portion 37, the semiconductor laser LD 38), and the optical unit 40 (41, 42, 43 and 44), a light emission unit for emitting the light of the predetermined wavelength region and transmitting the light to the light guide 26 is configured.

The other components of the endoscope system 1 are assumed to be almost similar to the components of the conventional and general endoscope system, and the illustration and description are omitted.

The action of the endoscope system 1 including the light source device for endoscope (the light source unit 12) in the present embodiment configured in this way will be described below.

Figure 2:
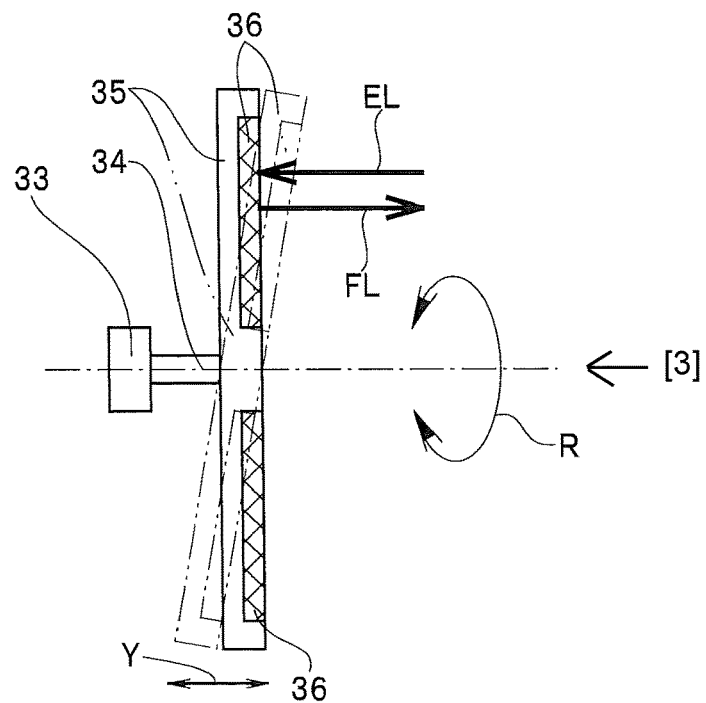
FIG. 2 is a conceptual diagram taking out, enlarging and illustrating a rotating body unit among components of the light source device for endoscope in FIG. 1.
Figure 3:
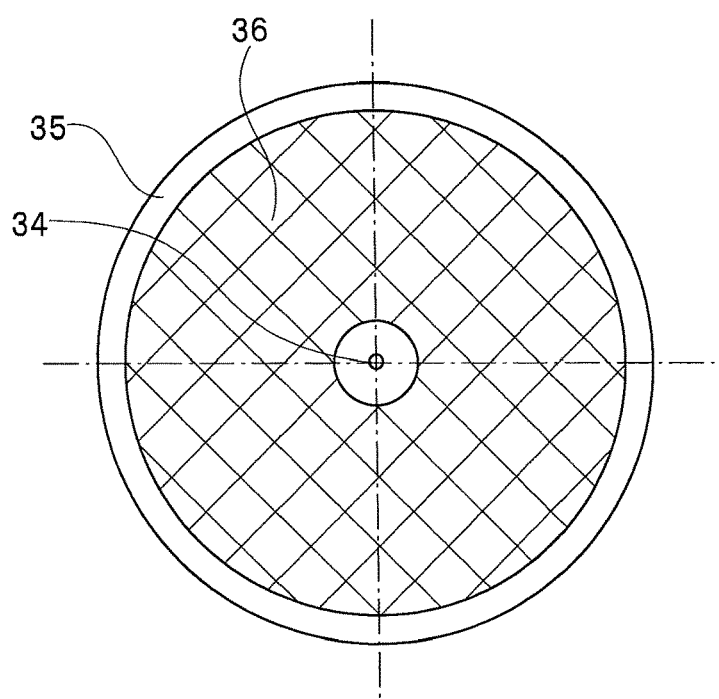
FIG. 3 is a diagram viewed in an arrow [3] direction in FIG. 2 and is a diagram illustrating a disposition board surface of a phosphor in a rotating body.
Figure 4:
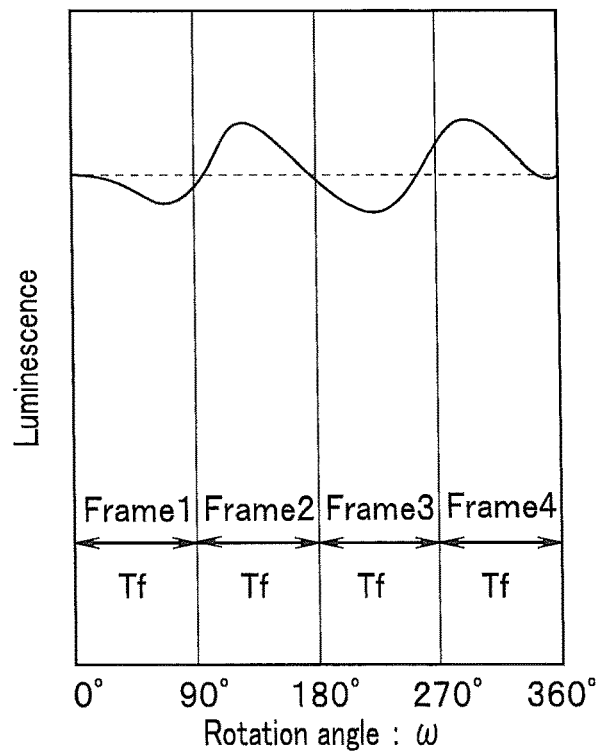
FIG. 4 is a diagram illustrating fluctuation of a light emission quantity of the phosphor in the rotating body, in the light source device for endoscope in FIG. 1.
Figure 5:
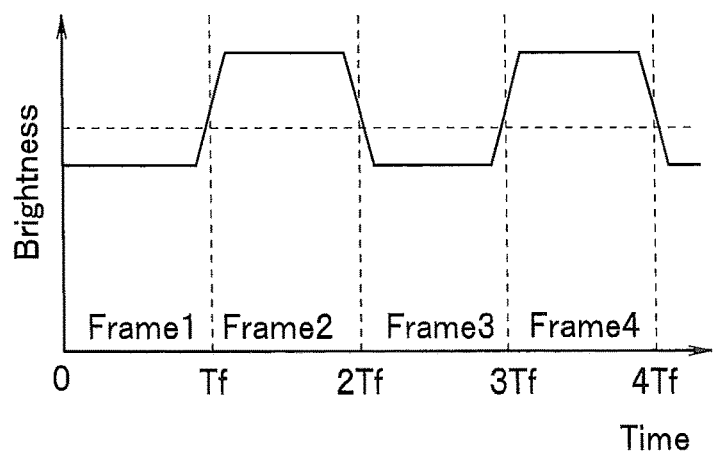
FIG. 5 is a graph illustrating brightness fluctuation of an image for each frame of the image acquired under a situation in FIG. 4.
Figure 6:
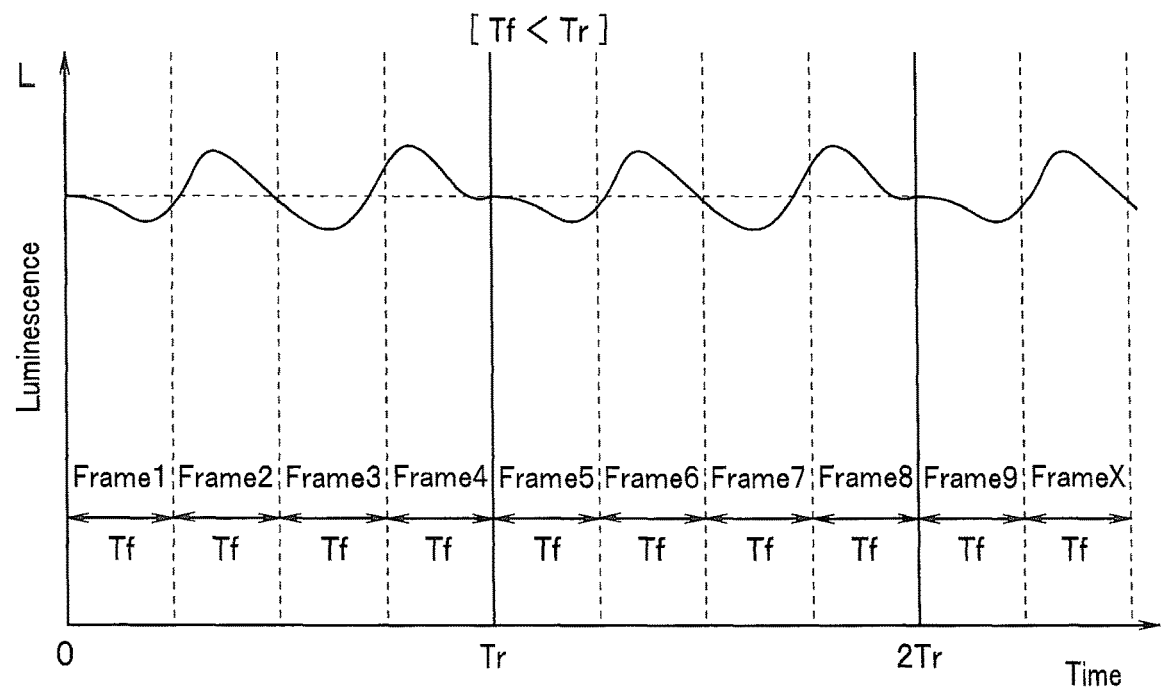
FIG. 6 is an illustration of a case of an image pickup cycle Tf<a rotation cycle Tr, illustrating a relation between the image pickup cycle Tf and the rotation cycle Tr and influence of the brightness fluctuation of the image when a light quantity of the phosphor generated from the rotating body fluctuates, in the light source device for endoscope in FIG. 1.
Figure 7:
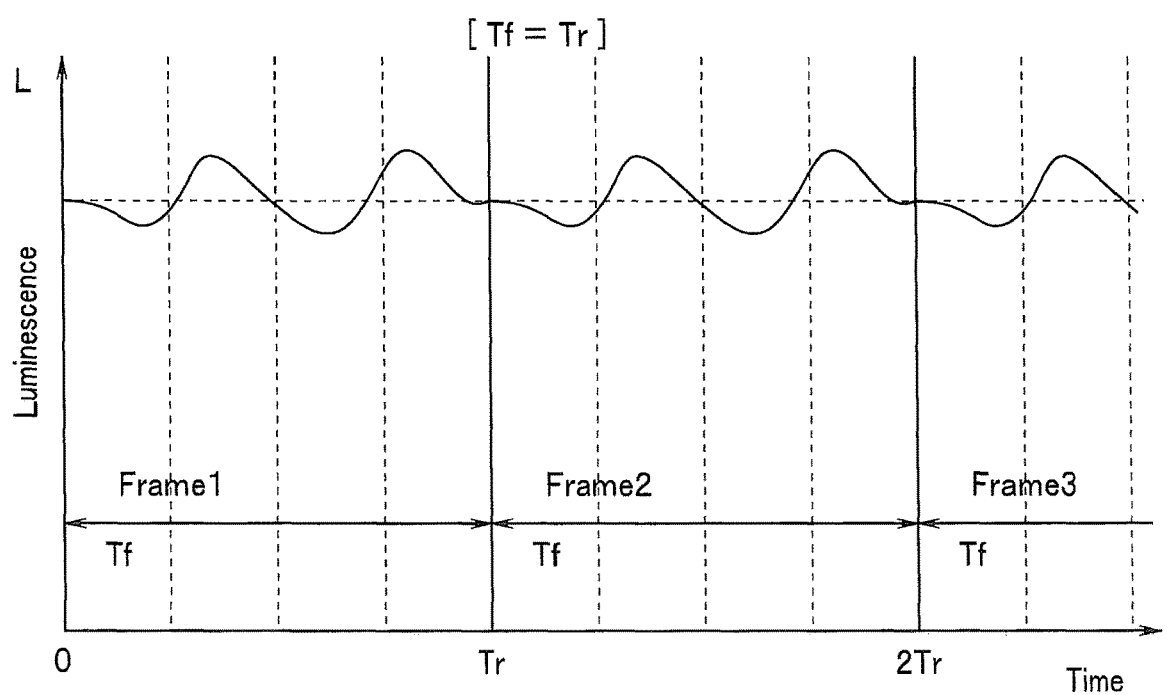
FIG. 7 is an illustration of a case of the image pickup cycle Tf=the rotation cycle Tr, similarly to FIG. 6.
Figure 8:
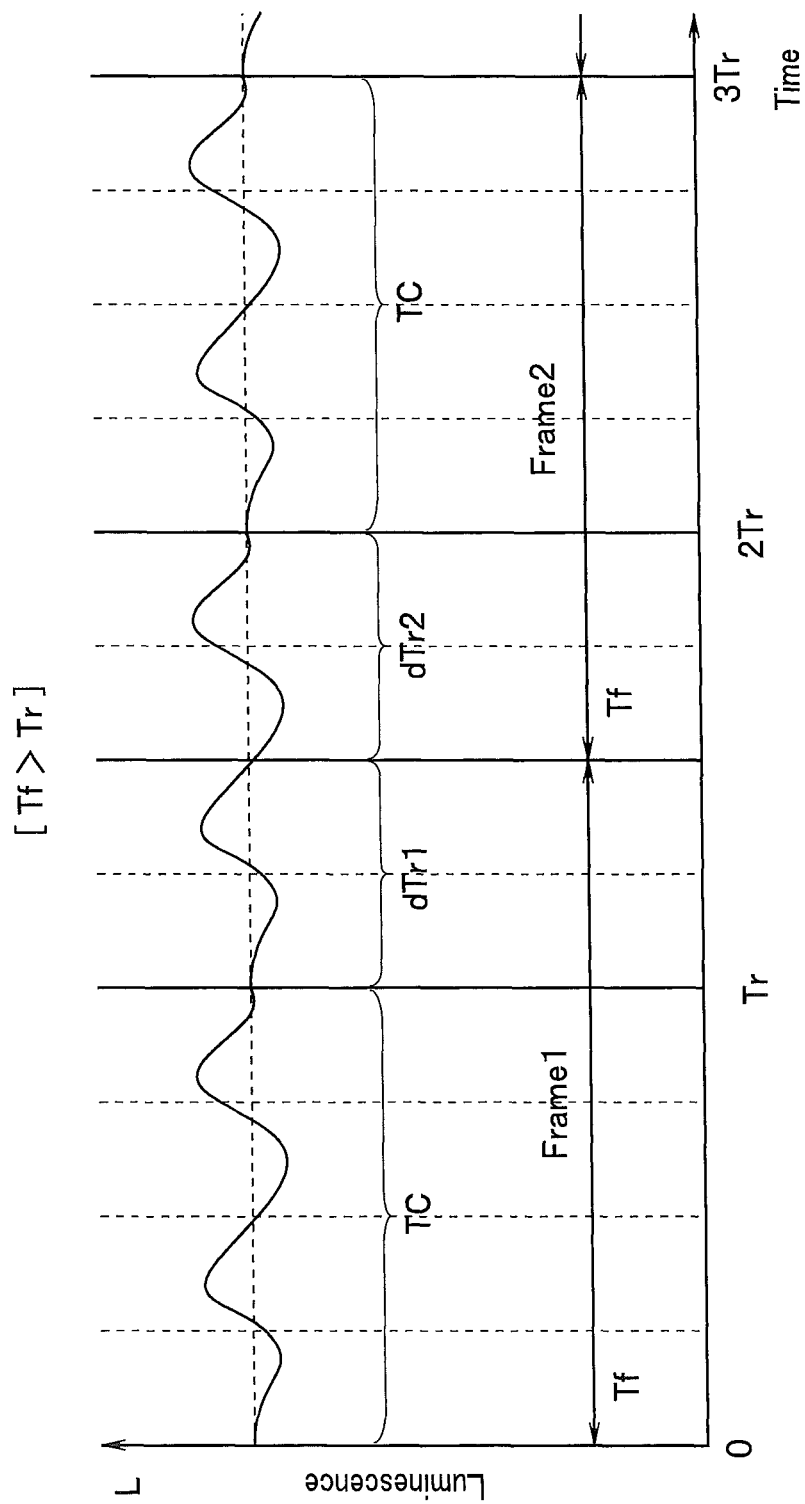
FIG. 8 is an illustration of a case of the image pickup cycle Tf>the rotation cycle Tr, similarly to FIG. 6.
Figure 9:
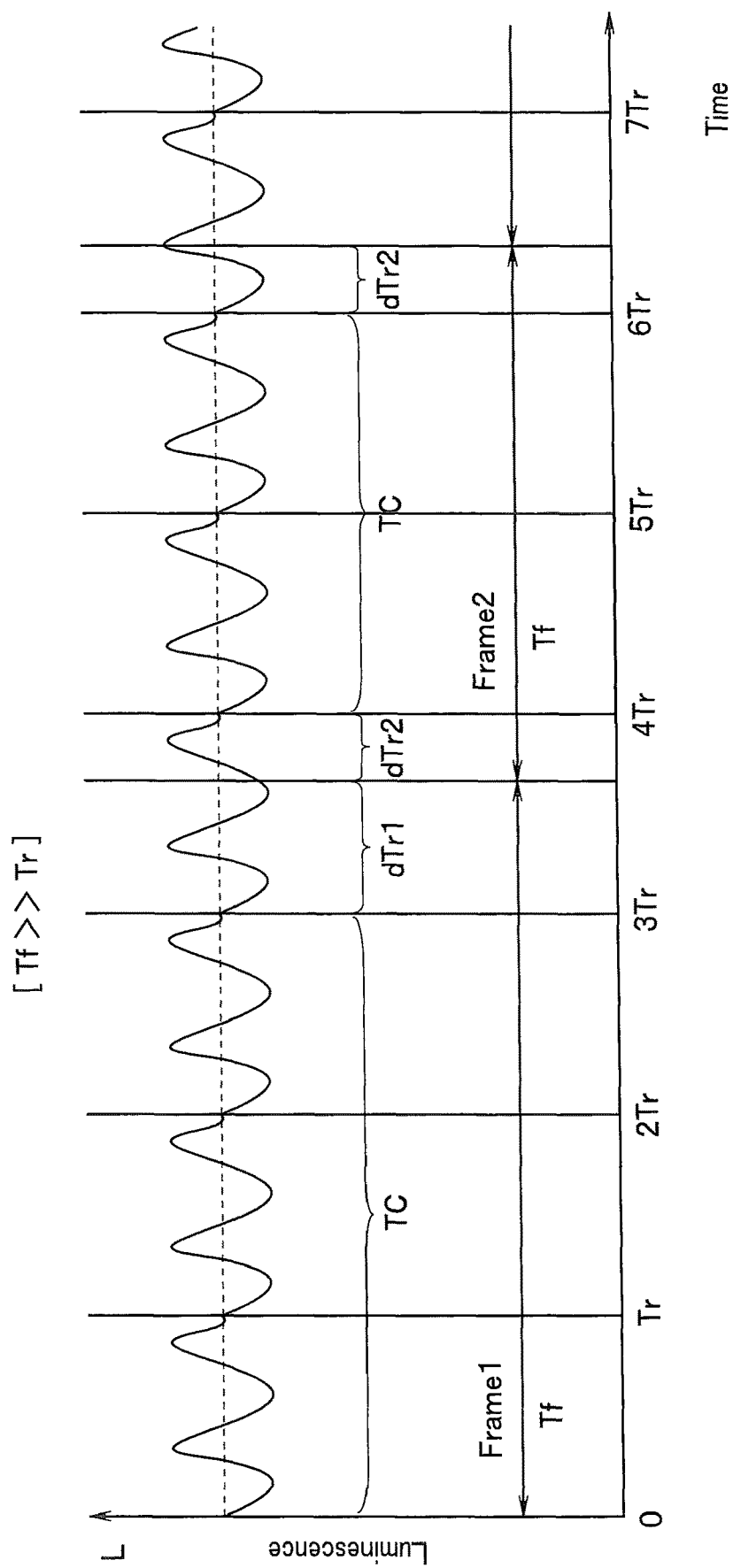
FIG. 9 is an illustration of a case of the image pickup cycle Tf>>the rotation cycle Tr, similarly to FIG. 6.

FIG. 2 is a conceptual diagram taking out, enlarging and illustrating the rotating body unit (the rotating body drive portion 32, the rotating body drive motor 33, the rotating body rotating shaft 34, the fluorescent wheel 35 (rotating body), the phosphor 36) among components of the light source unit 12 in the present embodiment. FIG. 3 is a diagram viewed in an arrow [3] direction in FIG. 2. That is, FIG. 3 illustrates a disposition board surface of the phosphor 36 in the fluorescent wheel 35 (rotating body). In addition, FIG. 4 is a diagram illustrating fluctuation of the light emission quantity (L; luminescence) of the phosphor in the fluorescent wheel (rotating body). FIG. 5 is a graph illustrating brightness fluctuation of an image for each frame of the image acquired under a situation in FIG. 4. FIG. 6 to FIG. 9 are graphs illustrating a relation between an image pickup cycle Tf and a rotation cycle Tr and influence of the brightness fluctuation of the image when the light quantity of the phosphor generated from the rotating body fluctuates. Among the figures, FIG. 6 is an illustration of a case of the image pickup cycle Tf<the rotation cycle Tr (note that the example in FIG. 6 is the same as FIG. 4). FIG. 7 is an illustration of a case of the image pickup cycle Tf=the rotation cycle Tr. FIG. 8 is an illustration of a case of the image pickup cycle Tf>the rotation cycle Tr. FIG. 9 is an illustration of a case of the image pickup cycle Tf>>the rotation cycle Tr.

The light source unit 12 in the present embodiment is configured to irradiate the phosphor 36 provided on the fluorescent wheel 35 (rotating body) with the irradiation light (excitation light; a sign EL in FIG. 2) from the semiconductor laser LD 38 (irradiation portion), and make the light (fluorescence; a sign FL in FIG. 2) of the predetermined wavelength region be emitted. In the case of such a configuration, due to various mechanical factors such as planarity of the disposition board surface of the phosphor 36 in the fluorescent wheel 35, board surface inclination based on attachment accuracy of the fluorescent wheel 35 to the rotating body rotating shaft 34, and rotational deflection of the rotating body rotating shaft 34, an irradiation position of the irradiation light (excitation light) EL from the semiconductor laser LD 38 (irradiation portion) to the phosphor 36 may vary. For example, in FIG. 2, the situation of the case where the board surface of the fluorescent wheel 35 is inclined is illustrated by a two-dot chain line. At the time, when the fluorescent wheel 35 is rotated around the rotating body rotating shaft 34 (in the direction of the arrow R), the rotational deflection of the fluorescent wheel 35 is generated in the direction of an arrow Y in FIG. 2.

As a result, the light emission quantity of the fluorescence FL from the phosphor 36 may vary. For example, as illustrated in FIG. 2, in the case where the board surface of the fluorescent wheel 35 is inclined, when the fluorescent wheel 35 is rotated, light quantity fluctuation of one cycle (for one round) is illustrated by a curve in FIG. 4 for example. In addition, besides the board surface inclination, the light emission quantity of the fluorescence FL may vary also due to formation irregularities (thickness irregularities or the like) of the phosphor, sticking of a foreign matter to the phosphor and a defect of the phosphor or the like.

Here, in FIG. 4, a sign "Frame1", a sign "Frame2", a sign "Frame3", and a sign "Frame4" indicate the image pickup cycle Tf. That is, FIG. 4 illustrates the example of the case of performing image pickup for four frames (4Tf) in one cycle Tr of the fluorescent wheel 35.

In this case, for the brightness of the image acquired and generated by the image pickup device, as indicated by the graph illustrated in FIG. 5, the brightness of the image varies with time due to a difference generated between the respective frames.

That is, examples of the case where the brightness of the image varies includes the case where the rotation cycle (Tr) of the rotating body is slow relative to the image pickup cycle (Tf) (Tf<Tr; the situation in FIG. 4 and FIG. 6), the case where the rotation cycle (Tr) of the rotating body is fast relative to the image pickup cycle (Tf) (Tf>Tr; the situation in FIG. 8), or the case where the rotation cycle (Tr) of the rotating body is sufficiently fast relative to the image pickup cycle (Tf) (Tf>>Tr; the situation in FIG. 9).

In the situation (Tf<Tr) in FIG. 4 and FIG. 6, dispersion of the rotating body is a direct cause of the light quantity fluctuation.

In addition, in the situation (Tf>Tr) in FIG. 8, a difference between a light quantity portion expressed by "dTr1" of the light quantity "TC+dTr1" of "Frame1" and a light quantity portion expressed by "dTr2" of the light quantity "TC+dTr2" of "Frame2" is the light quantity fluctuation between the frames.

Then, in the situation (Tf>Tr) in FIG. 9, similarly, a difference between the light quantity portion expressed by "dTr1" of the light quantity "TC+dTr1" of "Frame1" and a light quantity portion expressed by "dTr2+dTr2" of the light quantity "TC+dTr2+dTr2" of "Frame2" is the light quantity fluctuation between the frames. In this case, since a ratio of light quantity difference parts (dTr1, dTr2) to parts where the light quantity is in common (parts indicated by a sign TC) becomes proportionally small according to the rotation cycle, the light quantity fluctuation also tends to become small.

On the other hand, as means for suppressing the fluctuation of the brightness of the image, for example, the control of making the rotation cycle (Tr) of the rotating body that coincides with the image pickup cycle (Tf) (Tf=Tr; see FIG. 7) is conceivable. In this case, the image pickup cycle Tf and the rotation cycle Tr need to completely coincide, and complicated control is demanded.

In this way, in order to obtain stable and easy-to-view endoscopic image in the case where the brightness of the image fluctuates between the respective frames, some means for correcting the light quantity fluctuation between the respective frames needs to be taken.

As described above, since a light quantity fluctuation amount changes according to the rotation number of the rotating body, it is recognized that the brightness fluctuation of the endoscopic image can be reduced by increasing the rotation number of the rotating body. In addition, increasing the rotation number of the rotating body also leads to suppression of acceleration of degradation of the phosphor provided on the rotating body. However, when high speed rotation is performed at all times, it may be a cause of degrading the rotating body drive motor 33.

In addition, in the case where the observation target is at a position relatively close to the distal end face of the distal end portion 21 of the endoscope 2 (during so-called near point observation), the observation can be performed with a small light quantity. Therefore, the light emission quantity of the excitation light of the semiconductor laser LD 38 is generally controlled to be the small light quantity. Furthermore, since a larger light quantity is needed in order to perform clear observation as the observation target becomes far from the distal end face of the distal end portion 21 of the endoscope 2, the light emission quantity of the excitation light of the semiconductor laser LD 38 is controlled to be the large light quantity.

Therefore, considering that, in the light source unit 12 in the present embodiment, the light source control portion 31 outputs a predetermined light quantity instruction signal based on the brightness of the endoscopic image detected by the brightness detection portion 11a. Receiving the light quantity instruction signal, the rotating body rotation number control portion 46 sets the rotation number to rotationally drive the fluorescent wheel 35, and controls the drive of the rotating body drive portion 32.

For example, during the near point observation, under the control of the light source control portion 31, the LD drive control portion 47 performs the control of reducing the light emission quantity of the excitation light by reducing the irradiation intensity or the irradiation time of the emission light (excitation light) of the semiconductor laser LD 38. In this case, under the control of the light source control portion 31, the rotating body rotation number control portion 46 performs the rotation control of reducing the rotation cycle of the fluorescent wheel 35 (rotating body) (that is, increasing the rotation number and accelerating the rotation). Thus, the brightness fluctuation of the endoscopic image during the near point observation is suppressed.

In addition, during the distant observation, under the control of the light source control portion 31, the LD drive control portion 47 performs the control of increasing the light emission quantity of the excitation light by increasing the irradiation intensity or the irradiation time of the emission light (excitation light) of the semiconductor laser LD 38. In this case, under the control of the light source control portion 31, the rotating body rotation number control portion 46 performs the rotation control of increasing the rotation cycle of the fluorescent wheel 35 (rotating body) (that is, reducing the rotation number and decelerating the rotation).

Generally, when the rotation number of the fluorescent wheel 35 (rotating body) is lowered (the rotation is decelerated), compared to the time when the rotation number is high (the rotation is fast), the brightness of the endoscopic image fluctuates. However, since irradiation is performed by the large light quantity during the distant observation, it is the situation where it is difficult to identify the brightness fluctuation of the endoscopic image. Therefore, under the situation (during large light quantity irradiation), the brightness fluctuation of the endoscopic image caused by reducing the rotation number of the fluorescent wheel 35 does not greatly affect visibility of the endoscopic image. Therefore, in this case, without degrading the visibility of the endoscopic image, by reducing the rotation number of the fluorescent wheel 35 (rotating body), a load of the rotating body drive motor 33 is reduced and the degradation can be suppressed.

Figure 10:
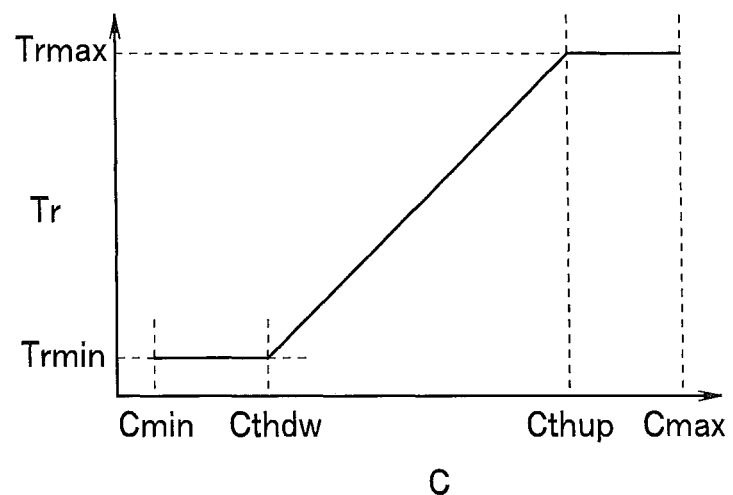
FIG. 10 is a graph illustrating one example of rotation number determination control by a rotation control portion in the light source device for endoscope in FIG. 1.

Here, one example of rotation number determination control by the rotating body rotation number control portion 46 will be simply described below. FIG. 10 is a graph illustrating one example of the rotation number determination control by the rotation control portion in the light source device for endoscope in the present embodiment.

In FIG. 10, a vertical axis is the rotation cycle Tr, and a horizontal axis is a light quantity instruction value C. As the rotation cycle Tr becomes larger, the rotation becomes decelerated. Therefore, for a maximum rotation cycle Trmax, the maximum rotation cycle capable of preventing the degradation of the phosphor 36 is set. In the maximum rotation cycle Trmax, a state that the rotation of the rotating body is the slowest is attained. In addition, for a minimum rotation cycle Trmin, a fastest rotation cycle on which the rotating body drive motor 33 can perform rotational drive is set. In the minimum rotation cycle Trmin, the state where the rotation of the rotating body is the fastest is attained.

The light quantity instruction value C is set in a range between a maximum light quantity instruction value Cmax and a minimum light quantity instruction value Cmin. Here, the maximum light quantity instruction value Cmax is the maximum light quantity value, and is the light quantity value when the semiconductor laser LD 38 is lighted by the maximum current value. In addition, the minimum light quantity instruction value Cmin is the minimum light quantity value, and is the light quantity value when the semiconductor laser LD 38 is lighted at the minimum current value.

Further, in FIG. 10, a threshold Cthup of the light quantity instruction value to be the maximum rotation cycle and a threshold Cthdw of the light quantity instruction value to be the minimum rotation cycle are set. Note that the threshold Cthup of the light quantity instruction value of the maximum rotation cycle may be the maximum light quantity instruction value Cmax. In addition, the threshold Cthdw of the light quantity instruction value of the minimum rotation cycle may be the minimum light quantity instruction value Cmin.

Note that, for the various kinds of parameters, data stored beforehand in a memory for temporary storage or the like provided inside the light source control portion 31 or the like is used for example.

In FIG. 10, a relational expression of the light quantity instruction value and the rotation number is expressed as $$Tr=(Cthup-Cthdw)/(Trmax-Trmin)*C.$$

As described above, according to the first embodiment, based on the brightness of the endoscopic image determined according to the light emission quantity of the semiconductor laser LD 38 or the phosphor 36, the rotating body rotation number control portion 46 controls the rotation cycle of the fluorescent wheel 35 (rotating body).

For example, during the near point observation (in the case of reducing the irradiation intensity or the irradiation time of the excitation light of the semiconductor laser LD 38), the rotating body rotation number control portion 46 can suppress the brightness fluctuation of the endoscopic image by performing the rotation control of reducing the rotation cycle of the fluorescent wheel 35 (rotating body) (accelerating the rotation).

In addition, during the distant observation (in the case of increasing the irradiation intensity or the irradiation time of the excitation light of the semiconductor laser LD 38), the rotating body rotation number control portion 46 can reduce the load of the rotating body drive motor 33 and suppress the degradation by performing the rotation control of increasing the rotation cycle of the fluorescent wheel 35 (rotating body) (decelerating the rotation). The brightness fluctuation of the endoscopic image generated at the time does not degrade the visibility of the endoscopic image.

Incidentally, the light source unit 12 (the light source device for endoscope) in the first embodiment described above is configured such that, for the light quantity control performed to make the endoscopic image displayed at the display device 4 have the predetermined brightness, that is, for the control of the light emission quantity of the excitation light of the semiconductor laser LD 38 (irradiation portion), the LD drive control portion 47 controls the irradiation intensity or the irradiation time of the excitation light based on the brightness of the endoscopic image detected by the brightness detection portion 11*a*.

However, the control of the light emission quantity of the excitation light of the irradiation portion is not limited to the example illustrated in the first embodiment, but may be by other means. For example, the configuration of controlling the light quantity of the excitation light using PWM (pulse width modulation) control of controlling ON/OFF of a drive current of the semiconductor laser LD 38 which is the irradiation portion is also conceivable.

In the case of using the PWM control in the light quantity control of the excitation light, the light quantity fluctuates according to a duty, that is, on-time. Therefore, the configuration may be such that the rotation cycle Tr of the rotating body drive motor 33 (the fluorescent wheel 35) is determined based on the duty (on-time).

As described above, the first embodiment is configured to, by the predetermined light quantity instruction signal outputted based on the brightness of the endoscopic image detected by the brightness detection portion 11*a*, such that the LD drive control portion 47 controls the light quantity of the semiconductor laser LD 38 through the LD drive portion 37, and the rotating body rotation number control portion 46 determines the rotation number to rotationally drive the fluorescent wheel 35 (rotating body). However, means of determining the rotation number of the fluorescent wheel 35 (rotating body) is not limited to the example but may be other means. A second embodiment of the present invention to be described next is a different illustration for the means of determining the rotation number of the fluorescent wheel 35 (rotating body).

Second Embodiment

The endoscope system including the light source device for endoscope in the second embodiment of the present invention will be described below. The configuration of the present embodiment is basically almost similar to the configuration of the first embodiment described above. The present embodiment is different from the first embodiment described above on the point that the light quantity of the excitation light emitted from the semiconductor laser LD 38 (irradiation portion) or the fluorescence generated from the phosphor 36 is detected and the rotation cycle of the rotating body is determined according to the light quantity detection result as the means of determining the rotation number of the fluorescent wheel 35 (rotating body). Therefore, in the present embodiment, only the components different from the components of the first embodiment described above will be described in details, and for the same components as the components of the first embodiment described above, same signs are attached and the description is omitted.

Figure 11:
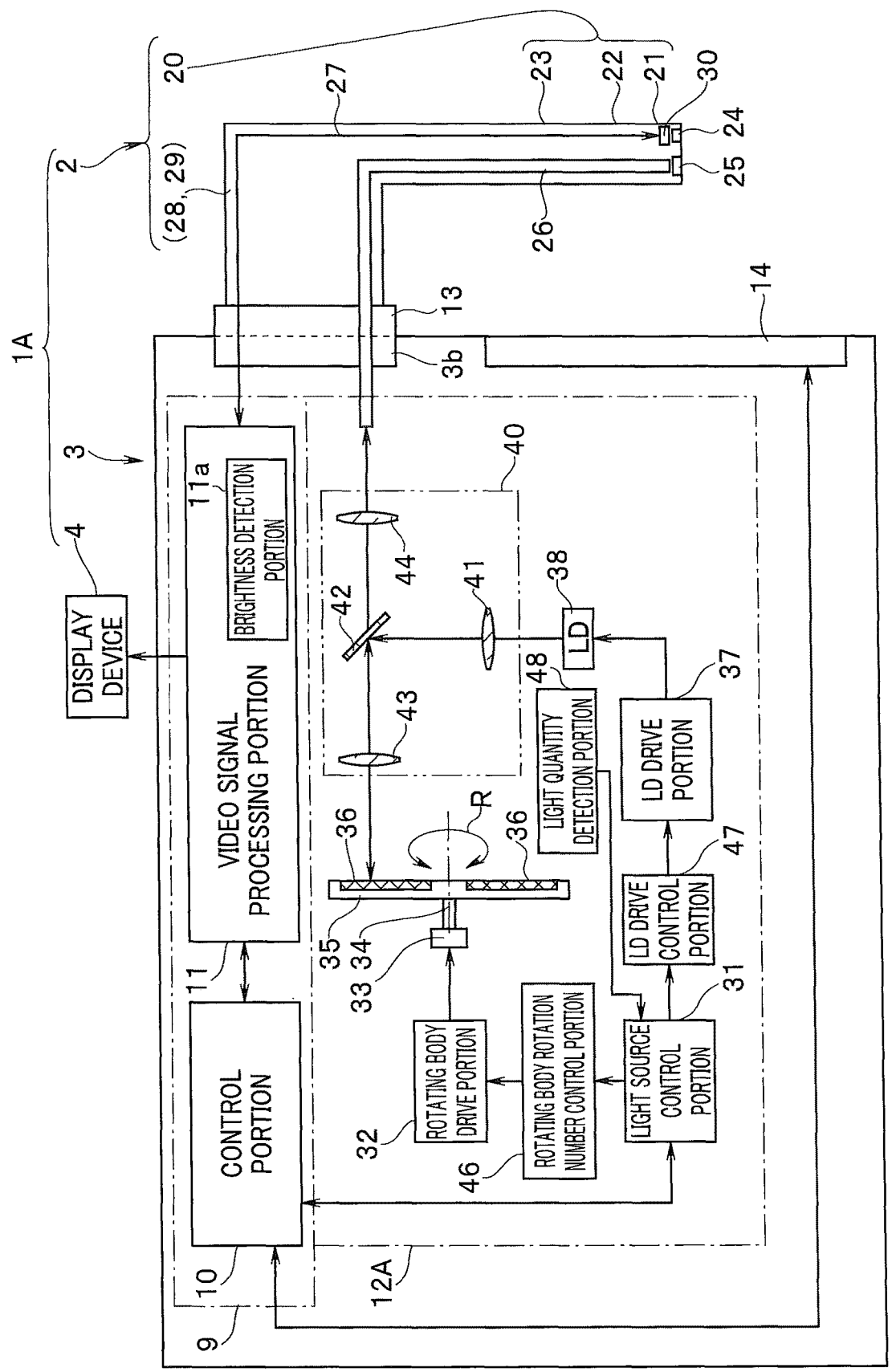
FIG. 11 is a block configuration diagram illustrating the schematic configuration of the endoscope system including the light source device for endoscope in a second embodiment of the present invention.

FIG. 11 is a block configuration diagram illustrating the schematic configuration of the endoscope system including the light source device for endoscope in the second embodiment of the present invention.

As illustrated in FIG. 11, in a light source unit 12A which is the light source device for endoscope in an endoscope system 1A in the present embodiment, a light quantity detection portion 48 which is light quantity detection means that detects the light quantity of the excitation light emitted from the semiconductor laser LD 38 (irradiation portion) or the fluorescence generated from the phosphor 36 is disposed.

In this case, the light quantity detection portion 48 is arranged near the semiconductor laser LD 38 or near the phosphor 36 for example. Then, the light quantity detection portion 48 is electrically connected with the light source control portion 31.

By such a configuration, a signal of the light quantity detection result by the light quantity detection portion 48 is outputted to the light source control portion 31. Receiving the signal, the light source control portion 31 outputs the predetermined light quantity instruction signal to the rotating body rotation number control portion 46 and the LD drive control portion 47. Receiving the light quantity instruction signal, the rotating body rotation number control portion 46 sets the rotation number to rotationally drive the fluorescent wheel 35, and controls the drive of the rotating body drive portion 32. In addition, the LD drive control portion 47 controls the drive of the LD drive portion 37, and controls the light quantity of the excitation light of the semiconductor laser LD 38. The other components and action are almost similar to the components and action of the first embodiment described above.

As described above, according to the second embodiment, effects almost similar to the effects of the first embodiment described above can be obtained.

Note that the light quantity detection means can also be similarly configured by means as follows, instead of the light quantity detection portion 48 described above. That is, instead of the means of directly detecting the light quantity of the excitation light emitted from the semiconductor laser LD 38 (irradiation portion) or the fluorescence generated from the phosphor 36 using the light quantity detection portion 48, the means of detecting magnitude of an LD drive current value is provided. Since the light quantity changes according to the LD drive current value, when the magnitude of the LD drive current value is detected, change of the light quantity is also detected. Therefore, the magnitude of the LD drive current value can be determined as the magnitude of the light quantity. In this way, the rotation cycle of the rotating body can be determined based on the magnitude of the light quantity according to the magnitude of the LD drive current value.

Third Embodiment

Next, the endoscope system including the light source device for endoscope in the third embodiment of the present invention will be described below. The configuration of the present embodiment is basically almost similar to the configuration of the first embodiment described above. The present embodiment is different from the first embodiment described above on the point that rotation number control in consideration of preventing the degradation due to temperature rise of the phosphor is performed when determining the rotation cycle of the fluorescent wheel 35 (rotating body). Therefore, in the present embodiment, only the components different from the components of the first embodiment described above will be described in details, and for the same components as the components of the first embodiment described above, the same signs are attached and the description is omitted.

Figure 12:
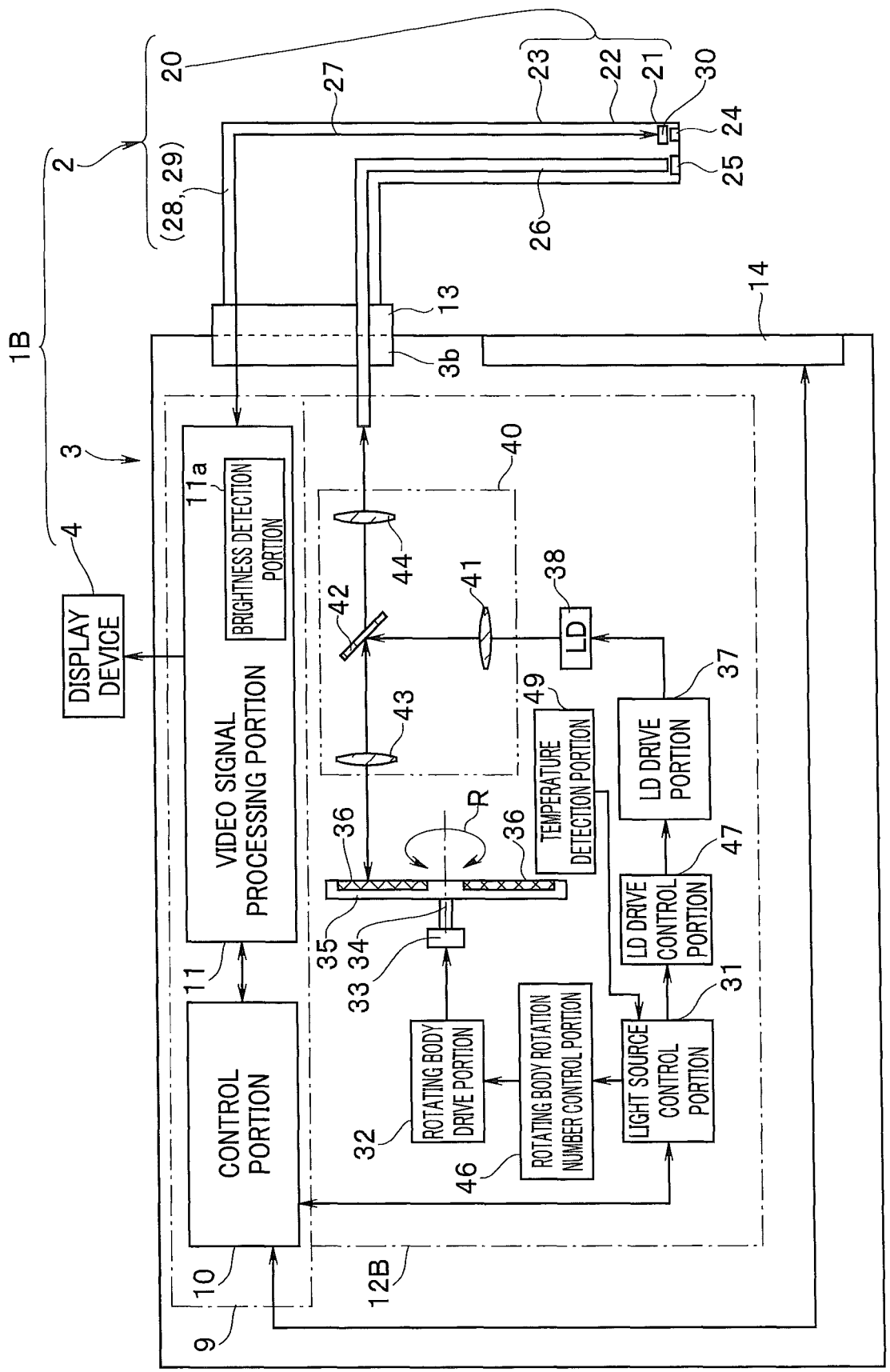
FIG. 12 is a block configuration diagram illustrating the schematic configuration of the endoscope system including the light source device for endoscope in a third embodiment of the present invention.
Figure 13:
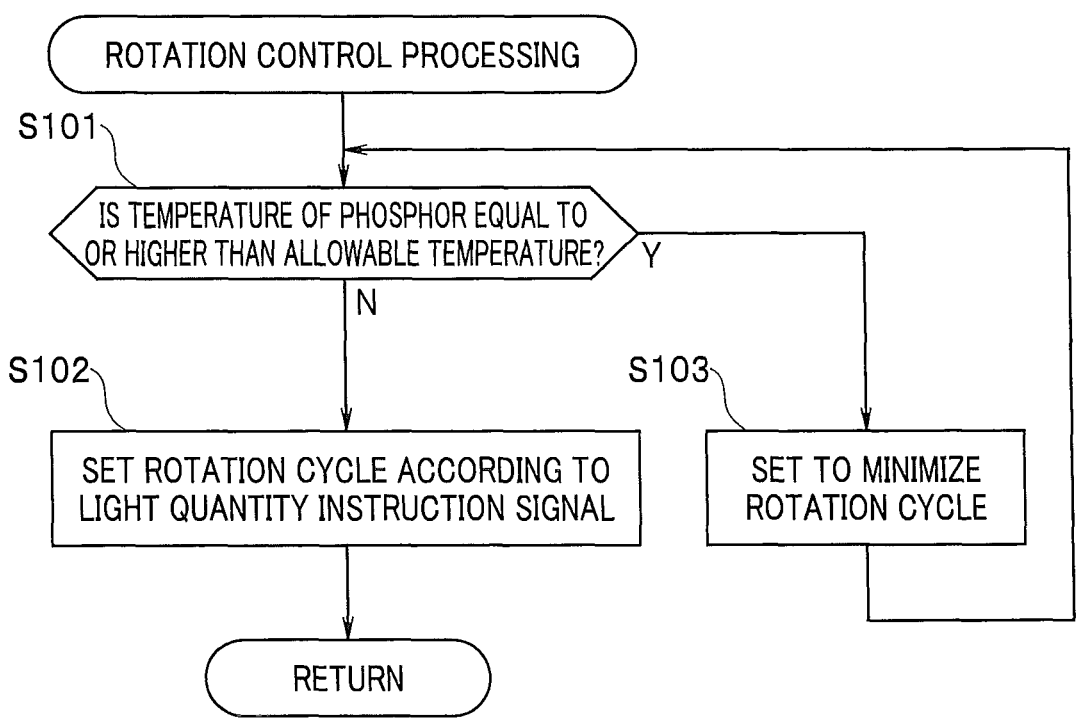
FIG. 13 is a flowchart illustrating a schematic flow of rotation number control processing in the light source device for endoscope in FIG. 12.

FIG. 12 is a block configuration diagram illustrating the schematic configuration of the endoscope system including the light source device for endoscope in the third embodiment of the present invention. FIG. 13 is a flowchart illustrating a schematic flow of rotation number control processing in the light source device for endoscope in the present embodiment.

As illustrated in FIG. 12, in a light source unit 12B which is the light source device for endoscope in an endoscope system 1B in the present embodiment, a temperature measurement portion 49 configured to measure a temperature of the phosphor 36 is disposed. In this case, the temperature measurement portion 49 is arranged near the phosphor 36 for example. Then, the temperature measurement portion 49 is electrically connected with the light source control portion 31.

By such a configuration, a signal of a temperature measurement result by the temperature measurement portion 49 is outputted to the light source control portion 31. Receiving the signal, the light source control portion 31 executes the rotation number control processing illustrated in FIG. 13.

First, in step S101, the light source control portion 31 determines the temperature based on the temperature measurement result received from the temperature measurement portion 49. In this case, when it is determined that the temperature measurement result of the phosphor 36 is below a predetermined allowable temperature, the processing advances to step S102. In addition, when it is determined that the temperature measurement result of the phosphor 36 is equal to or higher than the predetermined allowable temperature, the processing advances to step S103.

Here, the allowable temperature in the temperature measurement result is an upper limit value of the temperature at which the phosphor 36 is not degraded even when the phosphor 36 is exposed for a predetermined time period in the temperature environment.

Note that examples of factors causing the temperature rise of the phosphor 36 includes a fault of a cooling mechanism formed of a cooling fan or the like provided in order to cool the inside of the light source unit 12 and a fault of the rotating body drive motor 33 itself. Besides the factors, in the case where the excitation light of the semiconductor laser LD 38 acts on the phosphor 36 for example, specifically when the phosphor 36 is exposed to the excitation light of a high intensity (large light quantity) for a long period of time or in the case where the rotating body provided with the phosphor is rotated at a low speed or the like, the temperature of the phosphor 36 sometimes rises.

As described above, when it is determined that the temperature measurement result of the phosphor 36 is below the predetermined allowable temperature in the processing in step S101 and the processing advances to step S102, in step S102, the light source control portion 31 outputs the predetermined light quantity instruction signal outputted based on the brightness of the endoscopic image detected by the brightness detection portion 11a to the rotating body rotation number control portion 46 and the LD drive control portion 47. Receiving the signal, the rotating body rotation number control portion 46 sets the rotation number according to the inputted light quantity instruction signal, and controls the drive of the rotating body drive portion 32. In addition, the LD drive control portion 47 receives the light quantity instruction signal, controls the drive of the LD drive portion 37 according to the inputted light quantity instruction signal, and controls the light quantity of the excitation light of the semiconductor laser LD 38. Thereafter, the processing returns to an original processing sequence (return).

On the other hand, as described above, when it is determined that the temperature measurement result of the phosphor 36 is equal to or higher than the predetermined allowable temperature in the processing in step S101 and the processing advances to step S103, in step S103, the light source control portion 31 outputs the predetermined light quantity instruction signal to the rotating body rotation number control portion 46 and the LD drive control portion 47. Receiving the signal, the rotating body rotation number control portion 46 sets the rotation cycle to the settable minimum (Trmin) (that is, sets the rotation number to the settable highest), and controls the drive of the rotating body drive portion 32.

That is, in the case where the temperature measurement result of the phosphor 36 is equal to or higher than the predetermined allowable temperature, for example in the state where the phosphor 36 is irradiated with the excitation light of the large light quantity, when the rotation number of the fluorescent wheel 35 (rotating body) provided with the phosphor 36 is lowered, the temperature rises further. Then, in such a case (in the case where the phosphor 36 becomes equal to or higher than the predetermined allowable temperature), instead of the normal control based on the light quantity instruction signal, the rotation control of turning the rotation cycle Tr to the minimum (Trmin) is given priority. Then, the preferential control is executed until the phosphor 36 becomes lower than the allowable temperature.

In addition, in the processing in step S103, the LD drive control portion 47 receives the light quantity instruction signal, controls the drive of the LD drive portion 37 according to the inputted light quantity instruction signal, and controls the light quantity of the excitation light of the semiconductor laser LD 38. Thereafter, the processing returns to step S101 described above. Then, the similar processing is repeated until the temperature of the phosphor 36 becomes lower than the allowable temperature.

Note that the other components and action are almost similar to the components and action of the first embodiment described above.

As described above, according to the third embodiment, the effects almost similar to the effects of the first embodiment described above can be obtained.

Further, according to the present embodiment, by further providing the temperature measurement portion 49 configured to measure the temperature of the phosphor 36, when the phosphor 36 becomes equal to or higher than the predetermined allowable temperature (the upper limit value of the temperature at which the phosphor 36 is not degraded), the control different from the normal rotation control based on the light quantity instruction signal, that is, the control of turning the rotation cycle Tr to the minimum (Trmin) (turning the rotation number highest), is performed so that the degradation of the phosphor 36 can be prevented.

Fourth Embodiment

Next, the endoscope system including the light source device for endoscope in the fourth embodiment of the present invention will be described below. The configuration of the present embodiment is basically almost similar to the configuration of the first embodiment described above. The present embodiment is different from the first embodiment described above on the point that semiconductor light sources of a plurality of colors are provided and a plurality of observation modes can be coped with by switching an illumination light color by appropriately controlling the drive of the light source. Therefore, in the present embodiment, only the components different from the components of the first embodiment described above will be described in details, and for the same components as the components of the first embodiment described above, the same signs are attached and the description is omitted.

Figure 14:
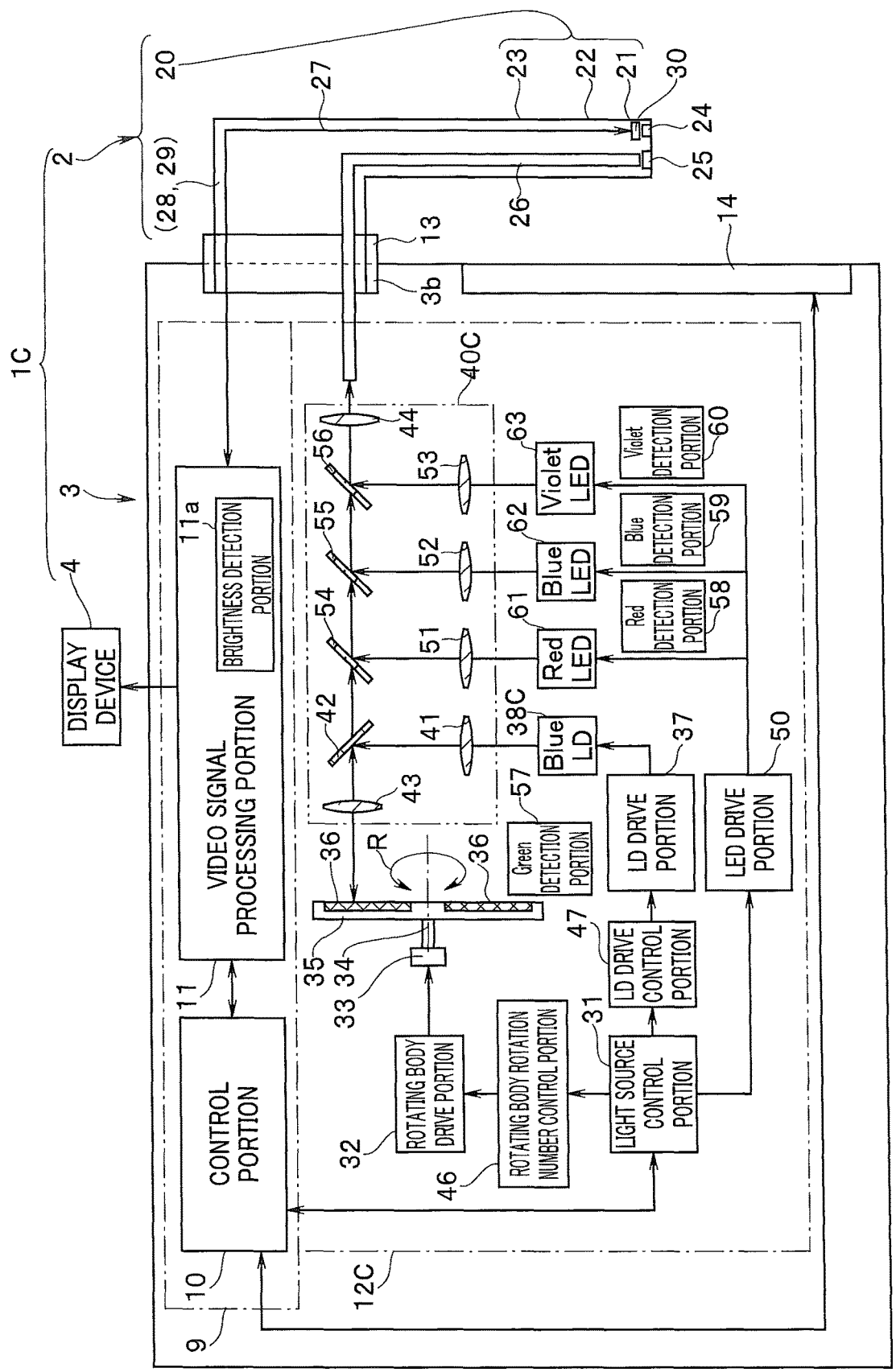
FIG. 14 is a block configuration diagram illustrating the schematic configuration of the endoscope system including the light source device for endoscope in a fourth embodiment of the present invention.

FIG. 14 is a block configuration diagram illustrating the schematic configuration of the endoscope system including the light source device for endoscope in the fourth embodiment of the present invention.

As illustrated in FIG. 14, a light source unit 12C which is the light source device for endoscope in an endoscope system 1C in the present embodiment is mainly configured by the light source control portion 31, the rotating body rotation number control portion 46, the rotating body drive portion 32, the rotating body drive motor 33, the rotating body rotating shaft 34, the fluorescent wheel 35 which is the rotating body, the phosphor 36, the LD drive control portion 47, the LD drive portion 37, a semiconductor laser blue LD (laser diode; abbreviated as Blue LD in FIG. 14) 38C which is the irradiation portion, an optical unit 40C, an LED drive portion 50, a plurality of LEDs (61, 62, 63) which are color light sources, and a plurality of color light source detection portions (57, 58, 59, 60) configured to detect the respective color light sources or the like.

Among the components, the semiconductor laser blue LD (Blue LD; irradiation portion) 38C, the optical unit 40C, the LED drive portion 50, the plurality of LEDs (61, 62, 63) and the plurality of color light source detection portions (57, 58, 59, 60) are different from the components of the light source unit 12 in the first embodiment described above.

The semiconductor laser blue LD (Blue LD; irradiation portion) 38C is the irradiation portion configured to radiate the excitation light, a blue laser beam in particular in the present embodiment. The irradiation light (excitation light) radiated from the semiconductor laser blue LD 38C is radiated to the phosphor 36 through the lens 41, the dichroic filter 42 and the lens 43 in the optical unit 40C. Then, the blue laser beam radiated to the phosphor 36 is reflected by the phosphor 36 and is then emitted to the proximal end face of the light guide 26 as green light through the optical unit 40C.

The plurality of LEDs (61, 62, 63; light emitting diodes) are a red LED 61 which is a light source configured to emit red light, a blue LED 62 which is a light source configured to emit blue light, and a violet LED 63 which is a light source configured to emit violet light.

The LED drive portion 50 is a drive circuit configured to generate an LED drive signal for driving each of the red LED 61, the blue LED 62, and the violet LED 63 and supply the LED drive signal to the respective color LEDs (61, 62, 63), by the control of the light source control portion 31.

The plurality of color light source detection portions (57, 58, 59, 60) are a green detection portion 57 configured to detect the green light of the fluorescence from the phosphor 36, a red detection portion 58 configured to detect the red light of the red LED 61, a blue detection portion 59 configured to detect the blue light of the blue LED 62, and a violet detection portion 60 configured to detect the violet light of the violet LED 63.

The optical unit 40C is configured including a plurality of lenses (41, 43, 44, 51, 52, 53) and a plurality of dichroic filters (42, 54, 55, 56).

Among the plurality of lenses, the lens 41 is an optical lens configured to transmit the irradiation light (excitation light) from the semiconductor laser blue LD 38C and emit the irradiation light to the dichroic filter 42.

Among the plurality of dichroic filters, the dichroic filter 42 is a planar optical member having a function of receiving the irradiation light (excitation light) from the semiconductor laser blue LD 38C transmitted through the lens 41, reflecting the irradiation light to the side of the phosphor 36, and also transmitting the light of the specific wavelength region of the irradiation light (fluorescence) from the phosphor 36 transmitted through the lens 43 as described later. The dichroic filter 42 is arranged by being inclined at the angle of 45 degrees relative to both of the optical axis of the lens 41 and the optical axis of the lens 43. In this case, so as to reflect the irradiation light (excitation light) from the semiconductor laser blue LD 38C to the side of the phosphor 36, the reflection surface is facing the side of the phosphor 36.

Among the plurality of lenses, the lens 43 is an optical lens configured to transmit the irradiation light (excitation light) from the semiconductor laser blue LD 38C that is reflected by the dichroic filter 42, transmit the irradiation light (fluorescence) from the phosphor 36, guide the irradiation light to the phosphor 36 and emit the irradiation light to the side of the dichroic filter 42.

Among the plurality of lenses, the lenses 51, 52 and 53 are optical lenses configured to transmit the irradiation light from the respective color LEDs (61, 62, 63) and emit the irradiation light to the respective reflection surfaces of the respective corresponding dichroic filters (54, 55, 56). Respective rays of the color light (red light, blue light, violet light) reflected by the respective dichroic filters (54, 55, 56) are converged by the lens 44 and emitted to a proximal end face of the light guide 26.

Among the plurality of dichroic filters, the dichroic filters 54, 55 and 56 are planar optical members configured to receive the irradiation light from the respective color LEDs 61, 62 and 63 respectively transmitted through the respective lenses 51, 52 and 53, reflect the irradiation light in the proximal end face direction of the light guide 26, transmit the irradiation light (fluorescence) from the phosphor 36 and emit the irradiation light in the proximal end face direction of the light guide 26.

Among the plurality of lenses, the lens 44 is an optical lens configured to converge and transmit the irradiation light (fluorescence) from the phosphor 36 advancing straight through the lens 43 and the dichroic filters 42, 54, 55 and 56 and emit the irradiation light toward a proximal end face of the light guide 26.

Note that, simply describing, in the light source unit 12C which is the light source device for endoscope in the present embodiment, by the rotating body unit (the rotating body drive portion 32, the rotating body drive motor 33, the rotating body rotating shaft 34, the fluorescent wheel 35 (rotating body), the phosphor 36), the LD unit (the LD drive portion 37, the semiconductor laser blue LD 38C), an LED unit (the LED drive portion 50, the red LED 61, the blue LED 62, the violet LED 63), and the optical unit 40 (41, 42, 43, 44, 51, 52, 53, 54, 55, 56), the light emission unit for emitting the light of the predetermined wavelength region and transmitting the light to the light guide 26 is configured. The other components are almost similar to the components of the first embodiment described above.

In the endoscope system 1C including the light source unit 12C in the present embodiment, for example, a plurality of observation modes (a normal light observation mode and a narrow band light observation mode, for example) according to different observation methods are provided. Note that the observation modes are not limited to the two observation modes described above, but may further include other observation modes.

Here, when a user operates the operation member (not illustrated) of the operation panel 14 and selects a desired observation mode, the instruction signal corresponding to the selected observation mode is outputted to the control portion 10. Note that observation mode selecting means here is not limited to the operation from the operation panel 14 but may be in the form of using the operation member (not illustrated) provided in the operation portion 28 of the endoscope 2 for example.

Among the plurality of observation modes, the normal light observation mode is an observation mode used in the case of performing observation in the illumination light of a wide wavelength band similar to normal white light by using the green light, red light and blue light of the fluorescence for example. In addition, the narrow band light observation mode is an observation mode capable of emphasizing a specific object such as a blood vessel in a surface layer of viable tissue and displaying the object as the endoscopic image by the illumination light of the predetermined wavelength band narrower than the wavelength band of the illumination light in the normal light observation mode by using the green light and the violet light of the fluorescence for example.

In the case where the normal light observation mode is selected as the observation mode, the control portion 10 controls the LD drive portion 37 and the LED drive portion 50 through the light source control portion 31 to drive the semiconductor laser blue LD 38C, the red LED 61 and the blue LED 62 and emit the irradiation light in the predetermined light quantity from the respective light sources. In addition, in the case where the narrow band light observation mode is selected as the observation mode, the control portion 10 controls the LD drive portion 37 and the LED drive portion 50 through the light source control portion 31 to drive the semiconductor laser blue LD 38C and the violet LED 63 and emit the irradiation light in the predetermined light quantity from the respective light sources. In these cases, the light source control portion 31 controls the drive of the LD drive portion 37 and the LED drive portion 50 so as to maintain a predetermined color balance.

Also in the fourth embodiment configured in this way, almost similarly to the first embodiment described above, by the light quantity instruction signal based on the brightness of the endoscopic image detected by the brightness detection portion 11a and the light emission quantity detected by the respective color light source detection portions 57, 58, 59 and 60, the rotation number control of the rotating body by the rotating body rotation number control portion 46 and the light quantity control by the LD drive control portion 47 are performed. Thus, the effects similar to the effects in the first embodiment described above can also be obtained in the present embodiment.

Fifth Embodiment

Next, the endoscope system including the light source device for endoscope in the fifth embodiment of the present invention will be described below. The configuration of the present embodiment is basically almost similar to the configuration of the first embodiment described above. The present embodiment is different from the first embodiment described above on the point that information of the endoscope is read and the rotation control of the rotating body is performed according to the connected endoscope. Therefore, in the present embodiment, only the components different from the components of the first embodiment described above will be described in details, and for the same components as the components of the first embodiment described above, the same signs are attached and the description is omitted.

Figure 15:
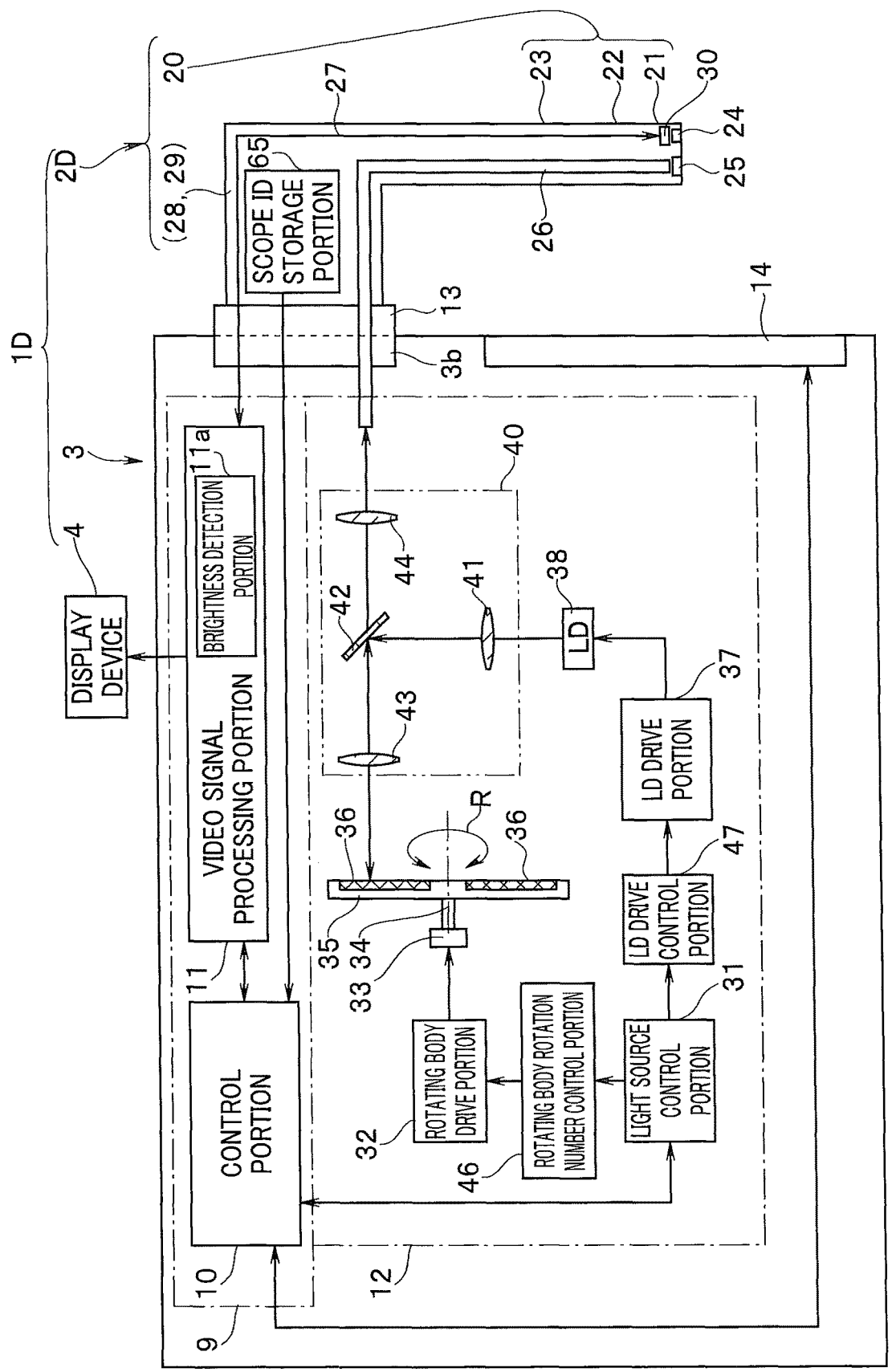
FIG. 15 is a block configuration diagram illustrating the schematic configuration of the endoscope system including the light source device for endoscope in a fifth embodiment of the present invention.

FIG. 15 is a block configuration diagram illustrating the schematic configuration of the endoscope system including the light source device for endoscope in the fifth embodiment of the present invention.

As illustrated in FIG. 15, in an endoscope system 1D in the present embodiment, a connected endoscope 2D is configured including a scope ID storage portion 65 in the operation portion 28 for example. As the scope ID storage portion 65, a storage medium such as a nonvolatile memory is applied for example.

In the scope ID storage portion 65, scope ID information including various kinds of information (referred to as endoscope information) intrinsic to the endoscope 2D or the like is stored beforehand for example. Here, the various kinds of the information (endoscope information) concerning the endoscope 2D illustrated as the scope ID information include a variety of the information such as scope kind information (kinds for respective applications concerning an observation part, specifically type information such as for stomach observation, for esophagus observation and for large intestine observation), kind information of the image pickup device used in the endoscope (such as the CCD or the CMOS), and a kind of an illumination light source. The other components are similar to the components of the first embodiment described above.

In the endoscope system 1D configured in this way, when the connector 13 of the desired endoscope 2D to be used is connected to the connector portion 3b of the control unit 3, the control portion 10 of the control unit 3 reads the various kinds of information from the scope ID storage portion 65 of the connected endoscope 2D, and executes the control for automatically setting the light emission quantity of the excitation light and the rotation cycle of the rotating body or the like suitable for the connected endoscope 2D through the light source control portion 31 of the light source unit 12. Then, in the light source unit 12, the light source control portion 31 performs the rotation number control according to a using situation such as the distant observation or the near point observation through the rotating body rotation number control portion 46.

As described above, according to the fifth embodiment, the effects almost similar to the effects of the first embodiment described above can be obtained. Further, according to the present embodiment, the connected endoscope 2D includes the scope ID storage portion 65 provided with intrinsic information such as the scope ID information. And when the endoscope 2D is connected, the required information is automatically read from the scope ID storage portion 65, and various kinds of settings are automatically performed concerning the appropriate light quantity control and rotation control for displaying the endoscopic image in the predetermined brightness based on the read information concerning the endoscope 2D. Thus, the system can be automatically set optimally for the connected endoscope 2D, and the excellent endoscopic image can be acquired at all times.

Note that the present invention is not limited to the embodiments described above, but of course various modifications and applications can be made without departing from the gist of the invention. For example, in addition to the red LED 61, the blue LED 62 and the violet LED 63, an amber LED which is a light source configured to emit amber light may be provided. Further, the embodiments include the inventions in various stages, and by appropriate combinations in a plurality of disclosed constituent elements, various inventions can be extracted. For example, even when some constituent elements are deleted from the entire constituent elements indicated in the one embodiment, in the case where the problem to be solved by the invention can be solved and the effect of the invention can be obtained, the configuration from which the constituent elements are deleted can be extracted as an invention. Further, the constituent elements over the different embodiments may be appropriately combined. The invention is not restrained by the specific embodiments other than being limited by attached claims.

The present invention can be applied to an endoscope control device in not only a medical field but also an industrial field.

What is claimed is:

1. A light source device for endoscope, comprising:
a light source capable of radiating excitation light;
a rotating body provided on an optical axis of the excitation light and configured to rotate with a rotating shaft as a center;
a phosphor arranged in an irradiation area of the excitation light in the rotating body, and configured to generate fluorescence by being irradiated with the excitation light; and
a controller configured to:
control irradiation intensity or irradiation time of the excitation light; and
rotate the rotating body at a predetermined speed when controlling the irradiation intensity or the irradiation time of the excitation light to be a first irradiation intensity or a first irradiation time,
rotate the rotating body faster than the predetermined speed when controlling the irradiation intensity less than the first irradiation intensity or controlling the irradiation time of the excitation light shorter than the first irradiation time; and
rotate the rotating body slower than the predetermined speed when controlling the irradiation intensity more than the first irradiation intensity or controlling the irradiation time of the excitation light longer than the first irradiation time.

2. An endoscope system comprising:
the light source device for endoscope according to claim 1; and
an endoscope including a light guide configured to guide the fluorescence generated from the phosphor and irradiate a subject with the fluorescence, and an image pickup sensor configured to receive light from the subject and generate an image pickup signal of the subject;
wherein the controller is further configured to:
generate an observation image of the subject from the image pickup signal of the subject generated by the image pickup sensor; and
detect brightness of the generated observation image,
control the irradiation intensity or the irradiation time of the excitation light in order to make the observation image have a predetermined brightness based on the detected brightness.

3. The light source device for endoscope according to claim 1, wherein
the controller is further configured to receive a light quantity detection signal indicating a detected light quantity of the excitation light radiated from the irradiation portion or a detected light quantity of the fluorescence generated from the phosphor,
wherein the controller rotates the rotating body slower than the predetermined speed when the detected light quantity of the excitation light or the detected light quantity of the fluorescence increases, and rotates the rotating body faster than the predetermined speed when the detected light quantity of the excitation light or the detected light quantity of the fluorescence decreases.

4. The light source device for endoscope according to claim 1, wherein
the controller is further configured to received a temperature measurement signal indicating a measured temperature of the phosphor,
wherein the controller controls a rotation speed of the rotating body based on the measured temperature when the measured temperature exceeds an allowable temperature at which degradation of the phosphor does not occur.

5. The light source device for endoscope according to claim 4, wherein the control of the rotation speed of the rotating body comprises rotating the rotating body more slowly than the predetermined speed.

6. The light source device for endoscope according to claim 1, further comprising
a motor configured to rotate the rotating body with the rotating shaft as the center,
wherein the controller controls the rotation speed of the rotating body to be equal to or lower than a highest rotation speed that the motor can drive and be equal to or higher than the rotation speed at which the phosphor is not degraded in a state where a light emitting portion emits the light at the maximum.

7. The endoscope system according to claim 2, wherein the endoscope further comprises a storage for storing endoscope information, and
the controller controls the irradiation intensity or the irradiation time of the excitation light in order to make the observation image have the predetermined brightness based on the predetermined endoscope information stored in the storage.

* * * * *